United States Patent

Thiem et al.

[11] Patent Number: 6,080,365
[45] Date of Patent: Jun. 27, 2000

[54] AUTOMATIC EMBEDDING MACHINE FOR TREATING SAMPLES FOR HISTOLOGICAL EXAMINATIONS, IN PARTICULAR FOR THE PREPARATION OF SECTIONS

[75] Inventors: Stefan Thiem, Heidelberg; Eric Barth, Leimen, both of Germany

[73] Assignee: Leica Instruments GmbH, Nussloch, Germany

[21] Appl. No.: 08/972,732

[22] Filed: Nov. 18, 1997

[30] Foreign Application Priority Data

Nov. 19, 1996 [DE] Germany .......................... 196 47 663

[51] Int. Cl.[7] .............................. B01L 3/00; B01L 11/00; B32B 27/04
[52] U.S. Cl. ............................ 422/99; 422/102; 422/103; 422/64; 422/65
[58] Field of Search .............................. 422/99, 102, 103, 422/64, 65, 66, 63, 62

[56] References Cited

FOREIGN PATENT DOCUMENTS

| | | |
|---|---|---|
| 878 871 | 6/1953 | Germany . |
| 1 038 795 | 9/1958 | Germany . |
| 1 097 164 | 1/1961 | Germany . |
| 1 114 338 | 9/1961 | Germany . |
| 1083511 | 1/1966 | United Kingdom . |
| 1405940 | 11/1972 | United Kingdom . |
| 1578029 | 7/1976 | United Kingdom . |

OTHER PUBLICATIONS

Histokinette, "Histokinette 2000", Rotary Tissue Processor, Leica Instruments GmbH, List 6008/ND/10/94, Oct. 1994 (Product Brochure).
Histokinette, "Histokinette 2000", Cambridge Instruments (Product Manual).

*Primary Examiner*—Jill Warden
*Assistant Examiner*—Dwayne K. Handy
*Attorney, Agent, or Firm*—Foley & Lardner

[57] ABSTRACT

A description is given of an automatic embedding machine (1) for treating samples for histological examinations, having a plurality of containers (4, 5) which are arranged one beside the other. The containers (4, 5) are each assigned an object holder (6), the object holders (6) being fastened on a turntable (7) provided over the containers (4, 5). The turntable (7) is connected to a central guide rod (8). The guide rod (8) is designed such that it can be moved perpendicularly with respect to the direction of rotation of the turntable (7). A vacuum device (9) for producing a vacuum in at least one of the containers (4, 5) is integrated in the automatic embedding machine (1).

9 Claims, 2 Drawing Sheets

AUTOMATIC EMBEDDING MACHINE FOR TREATING SAMPLES FOR HISTOLOGICAL EXAMINATIONS, IN PARTICULAR FOR THE PREPARATION OF SECTIONS

BACKGROUND OF THE INVENTION

The present invention relates to an automatic embedding machine for treating samples for histological examinations.

The preparation of tissue samples for histological examinations is carried out by a number of chemical treatments, and the samples are finally embedded in paraffin. For the chemical treatment, the water contained in the sample is first of all withdrawn from the latter and replaced by stabilizers, dyes and the like. Finally, the sample is embedded in paraffin. This means that the paraffin block can be retained in a stable manner in a receiving means of a microtome. So-called automatic embedding machines, which transport the samples automatically to the various treatment stages, have been developed for the various, successive process steps.

A known automatic embedding machine is described in the document "Jung HISTOKINETTE, Leica Instruments GmbH, List 6008/ND/10/94, October 1994". This automatic embedding machine contains a circular arrangement comprising a plurality of containers for chemicals as well as heatable containers for the wax. The containers are designed to be open at the top. Provided above the containers is a rotatable plate which has a plurality of sample-receiving means. The sample-receiving means can be introduced into the respective containers by virtue of the plate being lowered and rotated. Once a programmable period of time has elapsed, the plate, with the sample-receiving means, is raised again, rotated by a certain amount and lowered again into the next container.

In certain processing steps, it is necessary for a vacuum to be produced in the containers. In the "HISTOKINETTE", such a vacuum can only be produced by separate devices arranged outside the apparatus. These additional devices, however, make the apparatus more difficult to handle. Moreover, in many cases, toxic substances are used for the chemical treatment of the samples. In particular when the samples are changed to the next container, toxic contamination of the surroundings may thus occur. The externally arranged vacuum devices prevent the apparatus from being fully encapsulated.

SUMMARY OF THE INVENTION

It is an object of the invention to overcome the aforementioned limitations of prior automatic embedding machines.

It is a further object of the present invention to provide an automatic embedding machine which facilitates handling of the machine during operation in conjunction with a vacuum device.

These objects and others are achieved according to the invention by providing an automatic embedding machine that includes a plurality of containers which are arranged one beside the other and are each associated with at least one object holder. A turntable is provided over the containers wherein at least one object holder is fastened to the turntable. A central guide rod to which the turntable is connected is moveable perpendicularly with respect to the direction of rotation of the turntable. The automatic embedding machine also includes an integrated device for producing a vacuum in at least one of the plurality of containers.

According to one feature of the invention, the vacuum device is arranged on the turntable.

According to another feature of the invention, the at least one object holder is equipped with a cover and the cover has a peripheral seal which fits onto the container associated therewith.

According to yet another feature of the invention, the cover has a connection to the vacuum device.

According to yet another feature of the invention, a valve for the vacuum device is provided on the turntable.

According to still another feature of the invention, the guide rod has a hollow interior, and a power cable for the vacuum device is arranged in the hollow interior of the guide rod.

According to another feature of the invention, two semicircular shaped housing shells are arranged one inside the other on the guide rod via a pivot bearing. In one embodiment, the two housing shells fully encapsulate the automatic embedding machine.

According to another feature of the invention, the automatic embedding machine further comprises an integrated suction-removal means and a filter device connected thereto.

According to another feature of the invention, the plurality of containers includes a first set of chemical containers and a second set of paraffin containers.

According to still another feature of the invention, the at least one object holder holds one or more samples for histological examination.

The specific arrangement of the vacuum device on the rotatable components of the automatic embedding machine advantageously means that there is no adverse effect on the functioning of the automatically operating embedding machine. Moreover, a plurality of object holders can be controlled via a single vacuum device.

As noted above, in one embodiment of the invention, the automatic embedding machine is encapsulated by two rotatably arranged housing half-shells. During operation, the interior of the automatic embedding machine with the containers is closed off completely. This encapsulation means that an integrated suction-removal means with connected filter device can operate effectively and, consequently, contamination of the surroundings by the samples and/or chemical substances used can be ruled out.

The rotatable housing half-shells, which are arranged one inside the other, can be displaced for sample changing or else for changing the respective containers. This also ensures advantageous handling of the automatic embedding machine.

BRIEF DESCRIPTION OF THE DRAWINGS

The invention will be explained in more detail, with reference to an exemplary embodiment, with the aid of the schematic drawings, in which.

DETAILED DESCRIPTION OF THE PREFERRED EMBODIMENTS

We hereby incorporate by reference the disclosure of our German Patent Application No. 196 47 663.1-52 filed Nov. 19, 1996.

Figure 1:
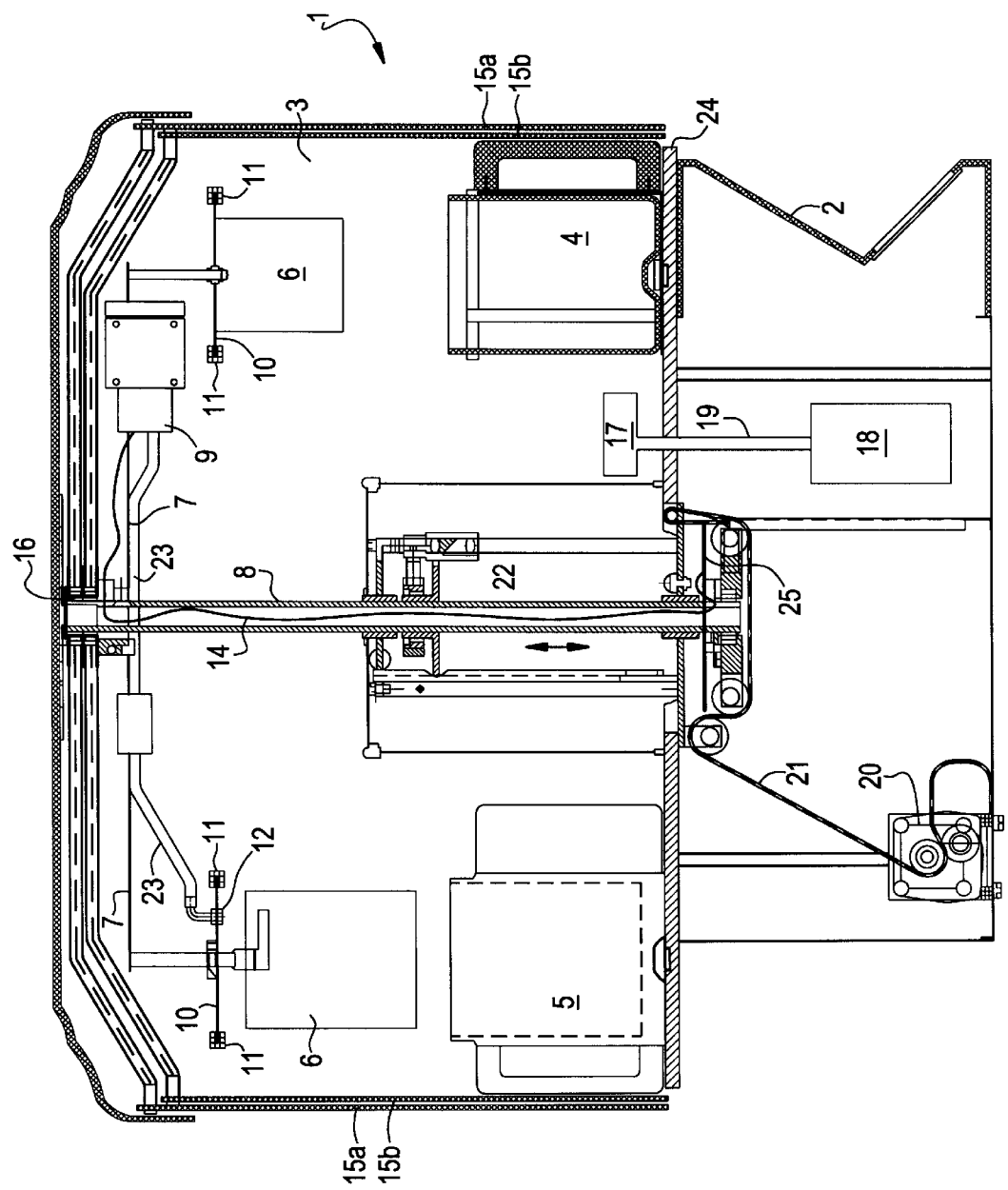
FIG. 1 is a sectional illustration of an automatic embedding machine in accordance with an embodiment of the invention.

FIG. 1 shows a sectional illustration of an automatic embedding machine 1 with a bottom housing part 2 and a top housing part 3, these two being designed to be separated from one another by a base part 24. A drive device 20 with a toothed belt 21 for a guide rod 8 is arranged in the bottom housing part 2. By virtue of the toothed belt 21 being moved via the drive device 20, the guide rod 8 can be raised and lowered again in the direction of the double arrow. Also arranged in the bottom housing part 2 is a filter device 18, which is connected, via a connecting line 19, to a suction-removal means 17 provided in the top housing part 3.

A plurality of chemical containers 4 arranged one beside the other and a plurality of paraffin containers 5 are provided on the base part 24. Fastened in the top region of the guide rod 8 is a turntable 7, which bears a plurality of object holders 6 for introduction into the respective containers 4 and 5. The object holders 6 are each equipped with a cover 10, and each cover has a peripheral seal 11. Once the object holders 6 have been introduced into the respective containers 4, 5, the latter are closed off in an air-tight manner by the seal 11. In order to produce a vacuum in the closed-off container 5, a vacuum pump 9 is arranged on the turntable 7, and this pump is joined to a connection 12 in the cover 10 via a vacuum tube 23 and a valve 13. The vacuum pump 9 is supplied with electricity via a power cable 14 which runs in the interior of the guide rod 8. The power cable 14 terminates in the bottom housing part 2 at an electrical slip-ring 25 of a power supply (not illustrated).

It is also possible for a plurality of object holders 6 to be connected to the valve 13 and/or to the vacuum pump 9.

Furthermore, a rotating device 22 for the guide rod 8 is provided in the top housing part 3. The rotating device 22 rotates the guide rod 8 by a certain angle during lowering, with the result that the object holders 6 are changed to the adjacent containers 4, 5.

For the purpose of encasing the automatic embedding machine 1, a first housing half-shell 15a and a second housing half-shell 15b are arranged at the top end of the guide rod 8. The housing half-shells 15a, 15b are arranged one inside the other and are designed such that they can be moved via a pivot bearing 16.

The two housing half-shells 15a and 15b are arranged by rotation during operation of the automatic embedding machine 1 such that the top part 3 is fully encapsulated. This also results in efficient utilization of the suction-removal means 17 with the filter system 18.

Figure 2:
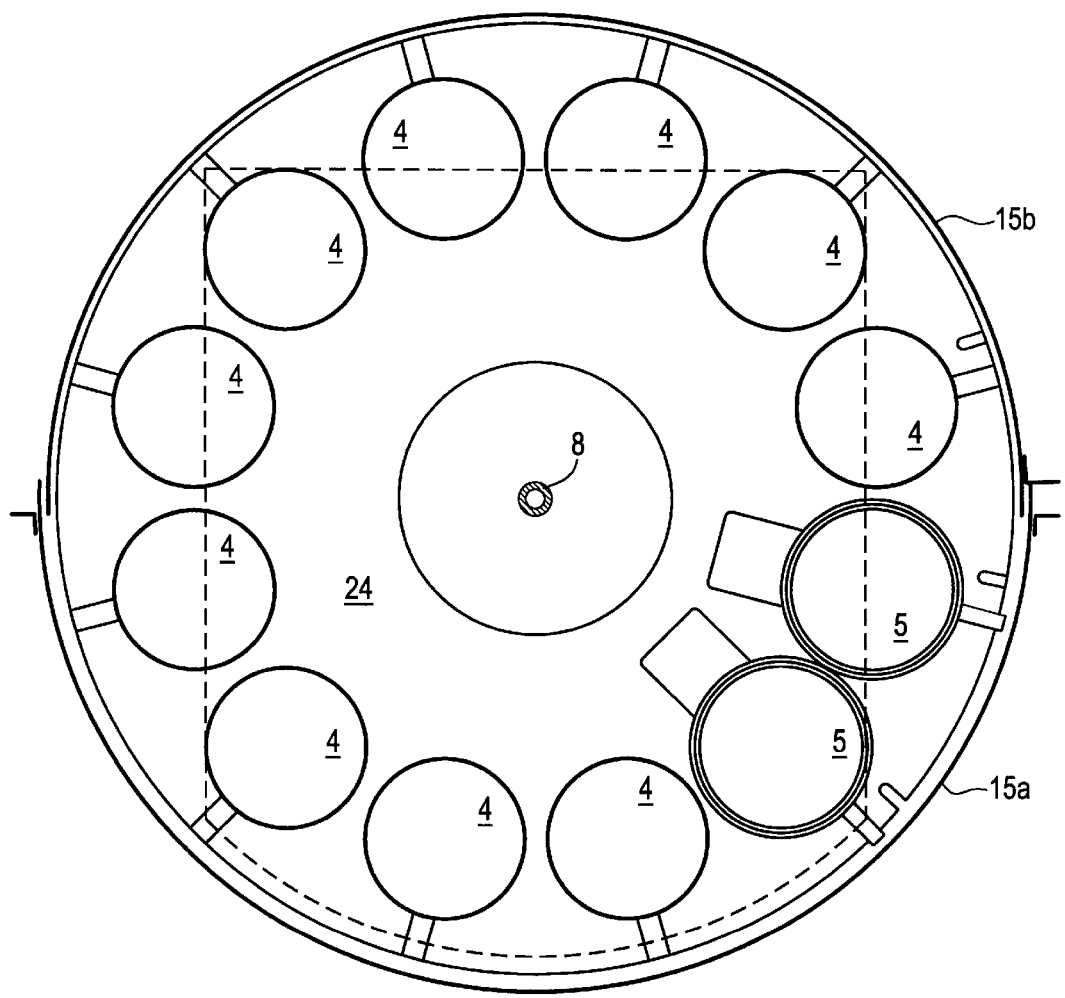
FIG. 2 is a plan view showing the containers of FIG. 1 arranged one beside the other in a circular arrangement.

FIG. 2 shows a plan view of the base part 24 with the containers 4 and 5 arranged one beside the other in a circular arrangement. It is clear from this illustration that a plurality of chemical containers 4 and a plurality of paraffin containers 5 are provided in the automatic embedding machine 1. The first housing half-shell 15a and the second housing half-shell 15b have been displaced with respect to one another, with the result that the automatic embedding machine 1 is fully encapsulated.

The invention has now been described in fulfillment of the foregoing objects by reference to a preferred embodiment. Various other embodiments and modifications will also be apparent to those skilled in the art without departing from the spirit and scope of the invention.

What is claimed is:

1. An automatic embedding machine for the treatment of specimens for histological study comprising:

a plurality of containers which are arranged one beside the other;

a turntable provided over the containers;

at least one object holder fastened to said turntable;

a central guide rod to which the turntable is connected, said guide rod being movable perpendicularly with respect to a direction of rotation of the turntable so as to move the at least one object holder relative to the plurality of containers; and an integrated vacuum device arranged on the turntable and connected to the at least one object holder, the vacuum device producing a vacuum upon introduction of the at least one object holder into the plurality of containers;

wherein the guide rod has a hollow interior, and a power cable for the integrated vacuum device is arranged in the hollow interior of the guide rod.

2. The automatic embedding machine as claimed in claim 1, wherein the at least one object holder is equipped with a cover, and said cover has a peripheral seal which fits onto the container associated therewith.

3. The automatic embedding machine as claimed in claim 2, wherein the cover has a connection to the integrated vacuum device.

4. The automatic embedding machine as claimed in claim 1, wherein a valve for the integrated vacuum device is provided on the turntable.

5. The automatic embedding machine as claimed in claim 1, wherein two semicircular shaped housing shells are arranged one inside the other on the guide rod via a pivot bearing.

6. The automatic embedding machine as claimed in claim 5, further comprising an integrated suction-removal means and a filter device connected thereto.

7. The automatic embedding machine as claimed in claim 5, wherein the two housing shells fully encapsulate the plurality of containers, the at least one object holder, and the integrated vacuum device.

8. The automatic embedding machine as claimed in claim 1, wherein the plurality of containers includes a first set of chemical containers and a second set of paraffin containers.

9. The automatic embedding machine as claimed in claim 1, wherein the at least one object holder holds one or more samples for histological examination.

* * * * *